United States Patent [19]

Arseneau

[11] 4,323,977
[45] Apr. 6, 1982

[54] NON-UNIFORMITY ENERGY CORRECTION METHOD AND APPARATUS

[75] Inventor: Roger E. Arseneau, Arlington Heights, Ill.

[73] Assignee: Siemens Gammasonics, Inc., Des Plaines, Ill.

[21] Appl. No.: 96,181

[22] Filed: Nov. 20, 1979

[51] Int. Cl.$^3$ .............................................. G01T 1/20
[52] U.S. Cl. .................................. 364/571; 364/414; 364/515; 250/363 S; 250/369
[58] Field of Search ............... 364/571, 414, 415, 515, 364/518, 521; 250/363 S, 369

[56] References Cited

U.S. PATENT DOCUMENTS

| | | | |
|---|---|---|---|
| 3,745,345 | 7/1973 | Muehllehner | 250/363 R |
| 3,872,434 | 3/1975 | DuVall et al. | 340/146.3 AG |
| 3,904,530 | 9/1975 | Martone et al. | 250/369 |
| 4,095,108 | 6/1978 | Inbar et al. | 250/363 S |
| 4,115,694 | 9/1978 | Lange et al. | 250/363 S |
| 4,151,416 | 4/1979 | Richey et al. | 250/363 S |
| 4,157,533 | 6/1979 | DuVall | 250/567 |
| 4,179,607 | 12/1979 | Lange et al. | 364/414 |
| 4,212,061 | 7/1980 | Knoll et al. | 364/571 |
| 4,223,221 | 9/1980 | Gambini et al. | 250/363 S |

FOREIGN PATENT DOCUMENTS

| | | | |
|---|---|---|---|
| 54-115184 | 9/1979 | Japan | 250/363 S |
| 54-136384 | 10/1979 | Japan | 250/363 S |

OTHER PUBLICATIONS

"Removal of Gamma Camera Non-Linearity and Non-Uniformities Through Real Time Signal Processing", G. F. Knoll, et al., Conference on Nuclear Medicine, France, Jul. 1979.
"Real-Time Correction of Radio-Isotope Camera Signals for Non-Uniformity and Non-Linearity", Knoll et al., Journal of Nuclear Medicine, vol. 19, p. 746, Jun. 1978.
"A New Method of Correcting for Detector Non-Uniformity in Gamma Cameras", Lapidus, Raytheon Medical Electronics, ST-3405, Nov. 1977.
"Digital Image Processing Applied to Scintillation Images from Biomedical Systems", IEEE Transactions on Medical Engineering, vol. BME-24, No. 4, pp. 337-347, Jul. 1977.
"Maximum a Posteriori Estimation of Position in Scintillation Cameras", Gray et al., IEEE Transactions on Nuclear Science, vol. NS-23, No. 1, pp. 849-852, Feb. 1976.
"The Non-Uniformity of Imaging Devices and its Impact in Quantitative Studies", Todd-Pokropek et al., Medical Radionuclide Imaging, vol. 1, pp. 67-84, 1977.
"Gamma-Camera Uniformity as a Function of Energy and Count-Rate", Hasman et al., British Journal of Radiology, 49, pp. 718-722, 1976.
"Scintillation Camera Nonuniformity: Effects on Cold Lesion Detectability", Tuinen et al., International Journal of Nuclear Medicine and Biology, vol. 5, pp. 140-144, 1978.
"Analysis and Correction of Spatial Distortions Produced by the Gamma Camera", Spector et al., Journal of Nuclear Medicine, vol. 13, No. 5, pp. 307-312, 1977.
"Field Flood Uniformity Correction: Benefits or Pitfalls?", Padikal et al., Journal of Nuclear Medicine, vol. 17, No. 7, pp. 653-656, 1976.
"Pitfalls in Gamma Field Uniformity Correction", Hannan et al., British Journal of Radiology, 47, pp. 820-821, 1974.
"Pitfalls in Gamma Camera Field Uniformity Correction", Jansson et al., British Journal of Radiology, 48, pp. 408-409, 1975.

*Primary Examiner*—Mark E. Nusbaum
*Assistant Examiner*—Gary Chin
*Attorney, Agent, or Firm*—Spellman, Joel & Pelton

[57] ABSTRACT

A method and apparatus are disclosed for correcting energy (Z) signal non-uniformities in the response of an Anger-type scintillation camera to image events occurring at different (X, Y) positions on the camera face. Energy correction factors f(P)' corresponding to deviations of up to ±12.8% from a reference pixel area are determined off-line for 4,096 camera face pixel areas from a uniform flood field source Z-map. The correction factors f(P)' are stored in a 64×64 array of a correction factor memory, addressable by image event (X, Y) position coordinates. During on-line operation, for each image event the correction factor $f(P)'$ corresponding to the image event $(X, Y)$ position is retrieved, scaled in a multiplying digital to analog converter by the actual energy $Z_{IN}$ of the event, and added to the event $Z_{IN}$ signal to provide a corrected energy signal $Z_c = Z_{IN}(1 + f(P)')$ which is proportional to the incoming signal. The corrected energy signal is then applied to a fixed energy window analyzer to determine acceptance or rejection of the event. The invention is especially advantageous for correcting energy non-linearities in the detection of single source with multiple energy levels and multiple sources with different energy levels.

10 Claims, 5 Drawing Figures

NON-UNIFORMITY ENERGY CORRECTION METHOD AND APPARATUS

BACKGROUND OF THE INVENTION

1. Field of the Invention

The present invention relates generally to the field of scintillation camera and image display forming apparatus and more particularly to a method and apparatus for correcting for the non-uniformities of energy distribution of scintillation cameras resulting in shifts in the energy distributions as a function of camera image field position.

2. Description of the Prior Art

Distortion in the image from image data obtained from scintillation cameras and associated image display apparatus is primarily due to spatial distortion and variations in point source sensitivity (image event energy signal non-uniformities). In presently available scintillation cameras of the "Anger-type", variations in point source sensitivity are maintainable to within 1-2% by means of elaborate component specifications, tuning and adjustment. Further, spatial distortion correction methods are known and more accurate correction methods are becoming available to correct for image events not being recorded by the scintillation camera apparatus in their correct image event locations with respect to the overall image and their position of original occurrence.

For example, one spatial distortion correction method is disclosed in U.S. Pat. No. 3,745,345 which issued to G. Muehllehner on July 10, 1973. Another, more accurate spatial distortion correction method and apparatus is disclosed in copending U.S. application Ser. No. 051,176 filed by E. W. Stoub et al on June 22, 1979. This more accurate spatial distortion correction method provides accurate repositioning of each event and corrects spatial distortion to obtain a corrected image having density variations of as low as 1% in response to a uniform field flood source.

The arrival of more accurate spatial distortion correction in scintillation camera images results in an increased attention to scintillation camera problems and improvements in the area of non-uniformities caused by energy variations in the energy distribution of image event signals as a function of position on the camera face; also known as point source sensitivity variations and image event energy signal non-uniformities.

While it is possible to control the image event energy non-uniformities in energy distributions in scintillation cameras to within 1-2%, this control is not practical for efficient manufacture and the costs of manufacture are much increased due to elaborate component specification and tuning procedures that must be performed. Further, the requirements for scintillation camera components such as the scintillation crystal of the camera detector head are rather stringent and the result is an increased cost of the crystal and a larger than desirable reject rate of the crystals.

Thus, appropriate design, component specifications and tuning can reduce energy non-uniformities to 1-2% for either slowly varying non-uniformity characteristics across the face of the crystal or constantly varying characteristics across the crystal face. However, crystal non-uniformities that exhibit either abrupt changes within small areas of the crystal or discontinuities are not capable of being tuned out or compensated for during manufacture.

When elaborate tuning is utilized as one element to obtain uniformity of the image event energy signals across the camera face, the camera is susceptible to detuning effects during the life of the camera such as to require frequent retuning during field life with resultant inconvenience and/or inaccurate image displays.

Another problem with the design, manufacture and tuning of the camera to achieve a low non-uniformity characteristic is the trade-off between camera characteristics such as point source non-uniformities, sensitivity, spatial distortion and resolution. The camera design characteristics that are required to achieve desirable uniformity in energy distribution across the image field of the camera result in the degradation of other important camera characteristics.

Scintillation cameras with corrected image density variations of 1% due to spatial distortion characteristics are only of value for diagnostic use when the non-uniformities due to energy variation are also accurately corrected since the variations in the image event energy signal if excessive cause an image event to be discarded if the image event energy signal does not fall within the energy window of the scintillation camera. The provision of a wider energy window of image event acceptance can result in the acceptance of image events that are caused by scattered radiation while still not achieving uniform acceptance of image events across the camera face.

Various methods to correct for the non-uniformities of scintillation cameras have been proposed. These methods are based on various attempts to vary the energy window against which each image event signal is compared to determine if the image event signal will be processed as a valid image event and displayed in accordance with the outputted X,Y image coordinates. These methods are sometimes referred to as "sliding energy window" techniques.

One method of energy window variation is described in a paper entitled "Removal Of Gamma Camera Non-Linearity And Non-Uniformities Through Real Time Signal Processing" by G. F. Knoll et al as presented at the Nuclear Medicine conference in Paris, France in July 1979.

The upper and lower extremes of a Z (energy) acceptance window are stored in a digital format at camera face array positions in a 64×64 format. Thus, when the X,Y position of an image event is produced by the camera, the corresponding upper and lower extremes of the acceptance window are read-out to a window comparison stage wherein the Z image event signal is compared to the programmed energy window.

Other studies discussing the use of non-uniformity corrections are "Sources of Gamma Camera Image Inequalities", Morrison et al, *Journal of Nuclear Medicine* 12: 785-791, 1971, and "A New Method Of Correcting For Detector Non-Uniformity In Gamma Cameras", Lapidus, *Raytheon Medical Electronics,* ST-3405, November, 1977.

The Lapidus article describes a method for modifying the Z (energy) signal of an image event by reading out a stored correction factor (from a 64×64 array) corresponding to the image event position. The correction factor varies the pulse width of the Z signal via a pulse width modulator to supply a variable pulse width Z signal. The display apparatus utilizes the variable pulse width Z signal to vary the intensity of the displayed image point on film. A flood mode is utilized to "learn" the distribution of non-uniformities. An array of values that represent the flood response of the camera detector at each of 4096 X-Y locations is then obtained and stored.

While the aformentioned prior art proposals and methods are generally suitable for their intended purpose and for studying non-uniformity response and effects, the previous systems, methods and proposals do not provide for modification of the energy of each image event signal to correct for non-uniform camera response and process the modified image event energy signals by a fixed energy window analyzer. Further, the prior art does not provide a system that is capable of automatically operating with different sources to correct for camera non-uniformities or with sources having multiple energy levels.

SUMMARY OF THE INVENTION

Accordingly, it is a principal object of the present invention to provide an improved method and apparatus to correct for the non-uniformity characteristics of scintillation cameras.

It is another object of the present invention to provide an improved method for determining energy correction factors as a function of image event position on the camera face, utilizing the stored energy correction factors in an on-line diagnostic phase to modify the image event energy signal of each image event by multiplying the image event energy signal by the corresponding correction factor, and comparing the modified image event energy signal with a predetermined fixed energy window to determine the acceptance or rejection of an image event.

It is a further object of the present invention to provide apparatus for modifying the image event energy signals of a scintillation camera in accordance with stored energy correction factors on an event by event basis and operating on energy signals representing scintillation events from sources having multiple energy levels.

Briefly and in accordance with one embodiment of the present invention, a method and apparatus is provided to correct the non-uniformities of energy distribution of scintillation cameras or the like caused by the variation in the energy distribution as a function of position on the camera face; i.e. field of view. The energy correction method accurately determines energy correction factors as a function of image event position in an off-line test, measurement and analysis phase prior to actual on-line diagnostic use. The energy correction factors are obtained from an energy map of image event data that is obtained during the test, measurement and analysis phase utilizing field flood image. The energy correction factors are stored in a predetermined addressable array format as a function of image event position and addressable by image event areas of the image field; an energy correction factor being stored in the array format corresponding to a predetermined area of the image event field. During the on-line use of the scintillation camera and associated image display system, the appropriate stored energy correction factor corresponding to each image event is read out to on-line energy correction apparatus. The on-line energy correction apparatus utilizes the image event energy signal and the corresponding stored energy correction factor to correct each image event energy signal. The corrected image event energy signal is supplied to a fixed width, energy window analyzer of the scintillation camera to determine the validity of the image event as determined by a comparison of the corrected image event energy signal and the energy acceptance range defined by the energy window characteristic of the energy window analyzer. The energy correction factors are obtained in the off-line test, measurement and analysis phase utilizing an energy source of a single energy level. The energy correction factors are utilized during on-line diagnostic use to automatically correct the image event energy signals for sources of different energy levels and also for sources having multiple energy levels without any adjustments or modifications to the scintillation camera.

These and other objects of the present invention will become apparent from the following detailed description taken in conjunction with the accompanying drawings.

DETAILED DESCRIPTION OF THE PREFERRED EMBODIMENT

Figure 1:
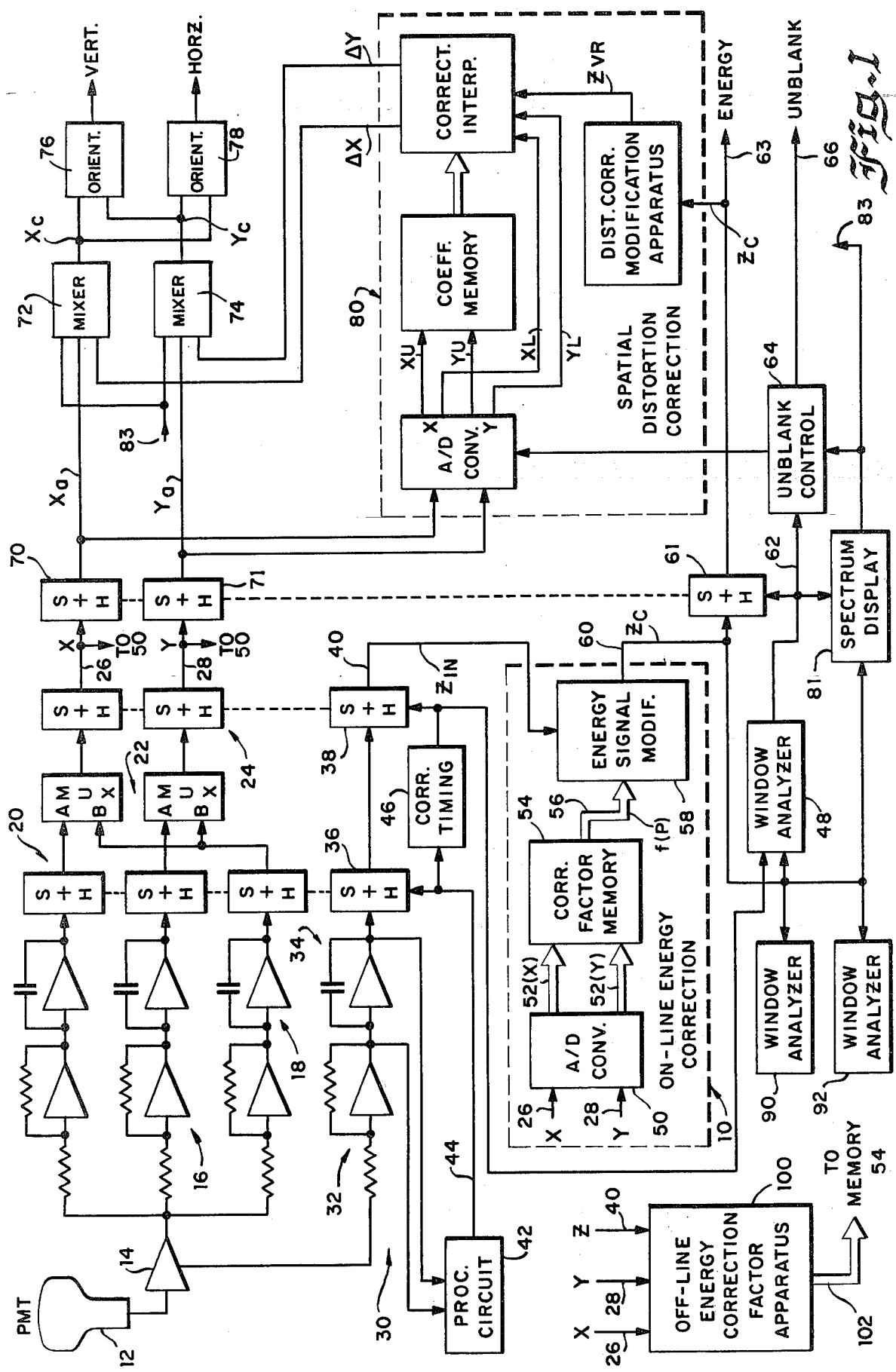
FIG. 1 is a schematic and block diagram representation of a scintillation camera and the non-uniformity energy correction method and apparatus of the present invention.

The on-line energy correction apparatus of the present invention utilized to practice the method of the present invention is referred to generally at 10 in FIG. 1 and is shown in connection with portions of a scintillation camera. The scintillation camera of FIG. 1 is of the general type that converts scintillation events into electrical signals that represent the position coordinates of each of the scintillation events and the energy of each of the scintillation events. The scintillation camera of FIG. 1 is an "Anger-type" camera well known in the scintillation camera field and as further described in U.S. Pat. Nos. 3,011,057, 3,745,345 and 3,984,689 to which reference may be made for a more detailed discussion of the general operation and detailed structure of a scintillation camera.

Figure 2:
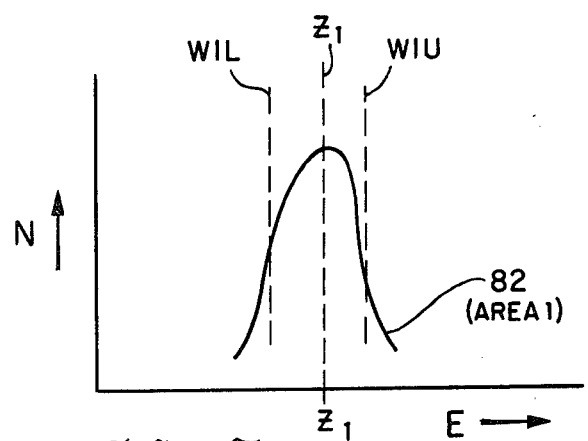
FIGS. 2, 3 and 4 are representations of energy distribution plots useful in explaining the operation of scintillation cameras and the requirements for the present invention.

Basically, scintillation events occur as radiation from gamma rays, for example, strike a scintillation crystal of the camera face. Photomultiplier tubes such as 12 of FIG. 1 are mounted in a predetermined array behind the scintillation crystal to convert the light energy of each scintillation event into an electrical pulse. In specific embodiments of scintillation cameras, a light pipe arrangement is provided between the crystal face and the photomultiplier tubes. In specific embodiments, 37 or 75 photomultiplier tubes as represented by PMT 12 are provided in the predetermined array to detect the scintillation events across the face of the scintillation crystal as shown in FIGS. 1 and 2 of the aforementioned U.S. Pat. No. 3,745,345.

In accordance with the detector electronics of scintillation cameras, the pulse outputs of the photomultiplier tubes in the array are connected through preamplifier stages referred at 14, sum and difference amplifier networks 16, integrator stages 18, sample and hold stages 20, multiplier stages 22, and sample and hold stages 24 as generally depicted in FIG. 1 to provide the X and Y position coordinates of each scintillation event. The output of each photomultiplier tube in the array depends on the proximity of the respective photomultiplier tube to the scintillation event.

The X coordinate output of the image event is referred to at 26 and the Y coordinate output of the image event is referred to at 28.

The output of the photomultiplier tubes such as 12 are also connected to a Z signal or energy analysis circuit 30. The Z signal circuit 30 includes a summing amplifier stage 32, an integrator stage 34 and two sample and hold stages 36 and 38. The output of the sample and hold stage 38 generates at 40 an uncorrected Z signal representing the energy of each image event as it occurs. The Z signal energy circuit 30 also includes a processing circuit 42 connected to the outputs of the summing amplifier 32 and the integrator 34 and producing an output at 44 to the sample and hold stage 36 and a correction and timing stage 46. The energy processing circuit 42 provides the function of an input coarse analyzer, early dump and pile-up processing as discussed in U.S. Pat. No. 3,984,689. The output of the correction and timing stage 46 is connected to the sample and hold stage 38 and a window analyzer stage 48. The X and Y position coordinate signals 26 and 28 and the Z energy signal 40 are connected as inputs to the energy correction apparatus 10.

The energy correction apparatus 10 includes an A to D converter stage 50 connected to the X and Y position coordinate outputs 26 and 28. The A to D converter stage 50 at output 52 converts each of the X and Y position coordinates for each image event into a digital output on a suitable number of digital control lines. The digital output 52 is connected to an address input of an energy correction factor memory 54 having stored therein a predetermined array of energy correction factors arranged to be addressed in accordance with image field position coordinate information representing areas or pixels of the camera face image field. The energy correction factors are determined in an off-line test, measurement and analysis phase and stored in the energy correction factor memory 54 for use during the on-line diagnostic use of the scintillation camera and associated apparatus.

During the on-line diagnostic use of the scintillation camera, each image event via the X and Y coordinate signals 26 and 28 digitally addresses the energy correction factor memory 54 by means of the analog to digital converter 50. Thus, in response to each image event, the energy correction factor memory 54 generates an output at 56 on a predetermined number of digital control lines in digital format that represents the predetermined energy correction factor to be appropriately applied to the energy signal at 40 from the corresponding image event in accordance with the pixel area at which the event occurred in the image area.

The digital correction factor referred to as f(P) at the output 56 of the energy correction factor memory 54 is connected to the input of an energy signal modification stage 58 of the energy correction apparatus 10. The Z signal 40 is also connected as input to the energy signal modification stage 58. In accordance with the digital correction factor f(P) at 56 and the analog Z (energy) signal at 40, the energy signal modification stage 58 at output 60 provides a corrected energy signal Zc in analog format. The corrected energy signal Zc at 60 is connected to the input of the window analyzer 48.

The window analyzer 48 compares the level of the corrected energy signal Zc at 60 for each image event with a predetermined energy window defined by upper and lower energy bounds. As a result of the comparison, the window analyzer 48 produces a first, predetermined accept output signal at output 62 when the corrected energy signal 60 is within the energy window set in the analyzer 48. Correspondingly, the window analyzer 48 at output 62 generates a second, predetermined reject signal when the energy signal is either above or below the energy window set in the window analyzer 48.

The output 62 of the window analyzer 48 is connected to an unblank control stage 64 that controls associated display and analysis apparatus over the unblank output 66. The unblank control stage 64 in response to the accept or reject signals on line 62 determines whether or not an image event is to be displayed or counted for analysis purposes.

The position coordinates of the event to be displayed are derived from the X and Y position coordinate information 26, 28 of each image event to control the displayed position of the image event in the image array produced by the associated display and analysis apparatus.

Specifically, the X position coordinate output 26 is connected through a sample and hold stage 70 as signal Xa to one input of a mixer and spectrum circuit 72. Similarly the Y position coordinate 28 is connected through a sample and hold stage 71 as signal Ya to one input of a Y mixer and spectrum circuit 74. The mixer and spectrum circuits 72 and 74 are selected from among known mixing and selector circuits. The outputs of the mixer and spectrum circuits 72 and 74 are each connected to one input of each of two conventional orientation circuits 76 and 78. The outputs of the circuits 76 and 78 are respectively connected to vertical and horizontal control lines that control the displayed position of the image event in the associated display and analysis apparatus. The orientation circuits provide for control of the orientation of the image reversing the X and Y position data to reorient the image by 180° for diagnostic purposes. A second input to the mixer and spectrum circuit 72 is connected to the output ΔX of a spatial distortion correction apparatus 80. Similarly, the Y mixer and spectrum circuit 74 includes a second input ΔY from the spatial distortion correction apparatus 80. A third input to each of the circuits 72 and 74 is connected to the output 83 of a spectrum display control stage 81 controlled by the output 62 of the window analyzer 48 and the corrected energy signal Zc at 60.

The spatial distortion correction apparatus 80 in accordance with predetermined spatial distortion correction factors stored therein modifies the Xa and Ya position coordinates of each image event to provide spatial distortion correction in the image display. Reference may be made to application Ser. No. 051,176 filed by E. W. Stoub et al on June 22, 1979 and application Ser. No. 096,182 filed by A. P. DelMedico on Nov. 20, 1979 for a more detailed description of the structure and operation of the spatial distortion correction apparatus 80.

During the on-line diagnostic phase, the energy correction apparatus 10 corrects the uncorrected Z energy signal 40 from the scintillation camera 10 in accordance with a correction factor f(P) to minimize the effects of the non-uniformity of energy response of the scintillation camera as a function of image event position about the camera face. In correcting for the non-uniform energy response of the scintillation camera, the energy correction apparatus 10 provides a corrected energy signal Zc at 60 to the energy window analyzer 48 to thus enable a valid decision to be performed to either accept or reject the image event in accordance with the corrected energy signal Zc by comparison to a predetermined fixed energy window. Thus, the corrected energy signal Zc is utilized by the window analyzer 48 to eliminate the effects of non-uniformity of camera response to avoid invalid rejections of image events or acceptances of undesired invalid image events.

To further understand the effects of energy and non-uniformity response of scintillation cameras and the operation of the energy correction apparatus 10, reference is made to FIG. 2 wherein there is illustrated the energy response of the scintillation camera as represented at the uncorrected energy signal output 40.

The plot of FIG. 2 represents energy along the abscissa and the number of events along the ordinate axis. The curve 82 represents an energy distribution or spectrum at a small predetermined pixel or area, area 1, of the camera face in response to a uniform field flood source for a period of time to obtain a statistically accurate sample. The energy distribution 82 is centered about a mean energy value Z1 and illustrates that most image events occur in a relatively narrow region above and below the mean value Z1 as in a gaussian distribution; e.g. the ordinate representing one-half of the peak of curve 82 corresponding to the ±6% energy range about Z1, the mean energy level. Thus, the plot 82 represents the response of the scintillation camera to a field flood source of radioactivity at one point or predetermined small area, area 1, of the camera face of the scintillation camera.

In accordance with non-uniformities of scintillation camera response over the camera face (at different points on the camera face), the energy distribution at these different points is similar in shape but centered around different mean energy levels. The variation in response or non-uniformity as discussed in the Background of the Invention is dependent on the manufacture and tuning of the camera.

Figure 3:
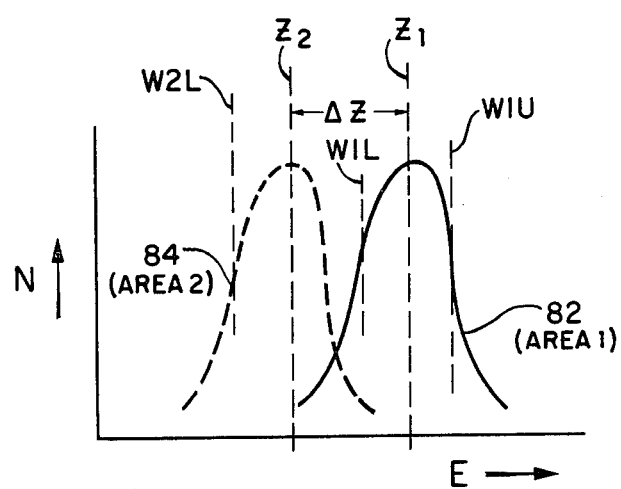

For example and referring now to FIG. 3, the energy distribution of curve 84 is shown in dashed line alongside the energy distribution plot 82. The energy distribution plot 84 represents the response of the camera at a different point or pixel area, area 2, of the camera face from that represented by the curve 82; the two curves 82 and 84 illustrating the non-uniformity of the response of the camera to image events occurring at two different points area 1 and area 2 on the camera face as represented by the difference ΔZ between the mean energy level Z1 of the distribution 82 and the mean energy level Z2 of the distribution 84.

In accordance with operation of the camera in diagnostic use, the level of the Z energy signal of each image event is compared to an energy acceptance window as discussed hereinbefore in connection with the window analyzer 48 and the image event energy signal. Thus, to determine the proper width of the energy window to be utilized in accepting and rejecting image events, the distribution of image events as energy distributions requires that the energy window be wide enough to include a high percentage of the events in the distribution to be statistically accurate and provide accurate imaging in diagnostic use and also suitable sensitivity to image events.

Thus, for example, in FIG. 2 an energy window is defined by the energy lines $W_1L$ and $W_1U$ which illustrate the respective lower and upper energy levels of the energy window for accepting image events; image events having energies that occur outside of this window being rejected and thus not displayed. Referring now to FIG. 3, it can be seen that if the image events of distribution curve 84 from Area 2 are compared to the energy window of level $W_1L$ and $W_1U$ defined by the distribution of Area 1, a substantial portion of the image events occurring at Area 2 will be rejected by the window analyzer 48. Thus valid image events will be discarded and the resulting image display will exhibit cold spots wherever the energy response of the camera differs substantially; e.g. response at Area 2 from that of the camera position Area 1 at which the energy window is defined. Accordingly, the non-uniformities of the camera response cause non-uniformities in the image display due to energy variations of camera response across different points on the camera face with each area of the camera face requiring a different energy window if valid image events are to be accepted and not erroneously rejected. In cameras without impractical manufacturing procedures and prohibitive component specifications, the total variation in response over the camera face is on the order of 5–10%.

Further, if the energy window of window analyzer 48 is opened sufficiently with upper and lower energy levels to accept substantial portions of all image events occurring in the various distributions across the face of the camera, such as denoted by lines $W_2L$ and $W_1U$, the energy window becomes rather wide. In diagnostic use, problems are encountered with such a wide energy window for accepting events.

Figure 4:
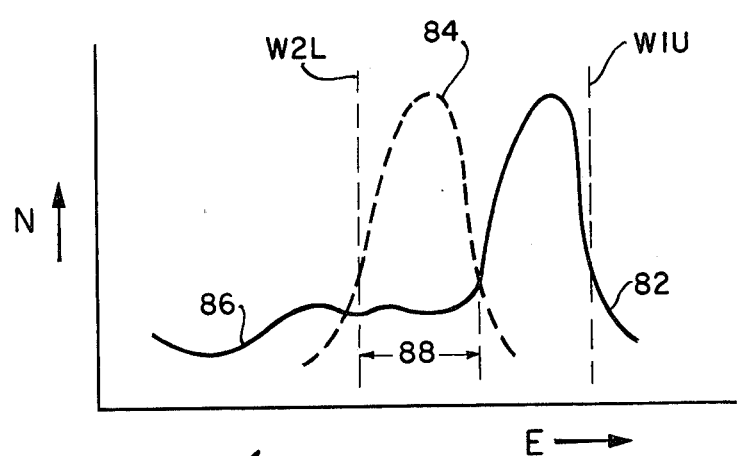

For example and referring now to FIG. 4, the energy distribution of curve 82 occurring at Area 1 of the camera face is now shown in a diagnostic environment and including a scatter portion of the energy distribution identified as curve portion 86. The scatter effects of curve portion 86, for example, are caused by radiation that occurs as an energy event of lowered energy levels at Area 1 of the camera face but originated from a different image field location; the gamma ray being deflected from its original direction with reduced energy, for example, by striking a bone or other portion of a patient. Thus, the scatter effects at curve portion 86 should be rejected by the scintillation camera 10 by means of the window analyzer 48 or distortion of the image will occur due to erroneous image events being displayed.

Thus, if the energy window of FIG. 3 represented by $W_2L$ and $W_1U$ were utilized to determine acceptance and rejection of image events, the scatter portion events of curve 82 in the range represented by 88 will be included as valid image event counts and displayed in the image. The result is an undesirable image display and erroneous hot areas of higher intensity due to the scatter.

As explained in the Background of the Invention, although it is possible to tune and design scintillation cameras so as to minimize the effects of non-uniformity of response to the extent that the energy variation is less than is shown in FIG. 3, such design and manufacture with elaborate tuning and rigid specifications of component parts is undesirable for efficiency of manufacture and for optimum performance in the field for diagnostic use.

In accordance with important aspects of the present invention, during an off-line test measurement and analysis phase, the non-uniformities of the camera as an energy response over the area of the camera face or image area are measured. Energy correction factors are calculated and stored for use in correcting the energy levels of each image event signal on an event by event basis in accordance with the appropriate stored energy correction factor for the area from which the image event occurred.

In effect, the energy correction apparatus 10, in on-line diagnostic use, shifts the energy distribution 84 from Area 2 event by event in accordance with the stored correction factor for Area 2 by the amount $\Delta Z$ such that the fixed energy window $W_1L$ and $W_1U$ can be utilized for window analyzer 48 to validly accept and reject image events as corrected for the non-uniformity of camera response with Area 1 representing a referenced point for energy level purposes and correction purposes of the camera.

Further, the energy correction factors are accurate for purposes of the correction of non-uniform camera response to sources of radiation having different energy levels from which the energy correction factors were first measured. Thus, the energy correction apparatus 10 during on-line diagnostic use can be utilized for sources of different energy levels and sources of multiple energy levels with separate window analyzers such as 90 and 92; the window analyzers 48, 90 and 92 having different predetermined fixed energy windows corresponding to the energy levels of the source to accept image events having different energy levels whether the image events are originating from sources having different energy levels of radiation or from a source having multiple energy level radiation.

Referring now to FIG. 1, the energy correction factors stored in the memory 54 are calculated during the off-line test, measurement and analysis phase using data acquired from a flood field source by off-line energy correction factor apparatus 100. The off-line energy correction factor apparatus acquires data from the X and Y position coordinate inputs 26 and 28 and the Z energy signal output 40 of the scintillation camera. An analysis of the image event data including a large number of events to obtain statistical accuracy generates the energy correction factors at output 102 to be stored in the memory 54 as an array of correction factors for corresponding pixels or small positional areas of the camera face.

Turning now to a more specific discussion of the calculation of the energy correction factors in the off-line test measurement and analysis phase, data memories of the off-line energy correction factor apparatus 100 tore the image events and energy of image event signals as they occur during the flood field analysis duration, which for example may include up to 20 million image events for statistical accuracy.

All of the image event data is stored in the data memories of the off-line energy correction factor apparatus 100 according to the coordinate position at which each event occurs. In one specific embodiment, the camera face or image area is divided into a pixel array of 64×64 with the effect that the camera face is divided into 4,096 pixel areas. Since scintillation camera faces are normally circular, a square array of 64×64 pixel areas result in some of the pixel areas in the square being outside the circular camera face area and thus unused. However, for designation and address purposes for data acquisition and analysis, pixel areas are organized by a square array of 64×64.

For each of the pixel areas, the total number $N_T$ of image events occurring at each pixel are counted and stored in a flood memory using, for example, 16 bits of information for storing the total image event counts for each pixel area. Further, the total energy of all events $Z_T$ occurring in each pixel throughout the analysis time are accumulated in a Z flood memory. Thus, at the end of the flood field source measurement, the off-line energy correction apparatus 100 has stored therein (for each pixel area by individual pixel area) the total number of image event counts per pixel area and the total energy of these events for each pixel area. For example, the Z-flood memory includes the total energy of all events occurring in one pixel area in twenty-four data bits. The data acquired from the flood field measurement is then utilized to calculate energy correction factors for each pixel area that are a measure of the non-uniformities of the camera response to uniform radiation impinging all pixel areas of the camera face with equal energy.

The off-line energy correction factor apparatus 100 from the stored data calculates the average energy per event Z map for each pixel area by dividing the contents of the Z-flood memory $Z_T$ by the flood memory contents $N_T$ as follows:

$$Z_{MAP} = \frac{Z_{FLD}}{N_T} \qquad (1)$$

From the $Z_{MAP}$ average energy per event data for each pixel, an energy correction factor f(P) is calculated that represents for each pixel area and as a percentage correction factor the amount by which the average energy $Z_{MAP}$ of the events for each pixel differs from the $Z_{MAP}$ of a reference pixel. The reference pixel in a specific embodiment is taken as the center pixel of the camera face and is designated in accordance with photomultiplier tube array designation as $Z_{19}=Z_{Ref}$. The correction factor f(P) is calculated as follows in terms of the variable f(P) having a center range of zero:

$$f(P)' = \frac{(Z_{19} - Z_{MAP}) \, 1000}{Z_{MAP}} \qquad (2)$$

Where the factor of 1000 represents a scaling factor in accordance with the parameters of the energy correction apparatus 10 and for ease of digital storage of the factors f(P) as binary numbers in an appropriate range in the on-line energy correction factor memory 54. For example, if f(P) is stored as a binary number of 8 bits representing a number from 0 to 255, the correction factor expressed as a percentage represents an energy variation $Z_{MAP}$ in the range of ±12.8% from the $Z_{Ref}=Z_{19}$, and the variable f(P)' represents a range of −128 to +127 with a zero center range value with f(P)=f(P)'+128.

The calculated values of f(P) for each pixel area are stored as a 64×64 addressable array of digital data in the on-line energy correction factor memory 54 of the on-line energy correction apparatus 10 as computed from the data of the off-line test, measurements and analysis phase. The 64×64 array represents at each array memory location, the factor f(P) for the corresponding pixel area. In a preferred embodiment, the correction factor f(P) is stored as a digital number from 0 to 255 corresponding to a range of the variable f(P)' of −128 to +127 about the reference denoted as zero. As stored, the reference value corresponds to a value of 128 in the range of 0 to 255.

Figure 5:
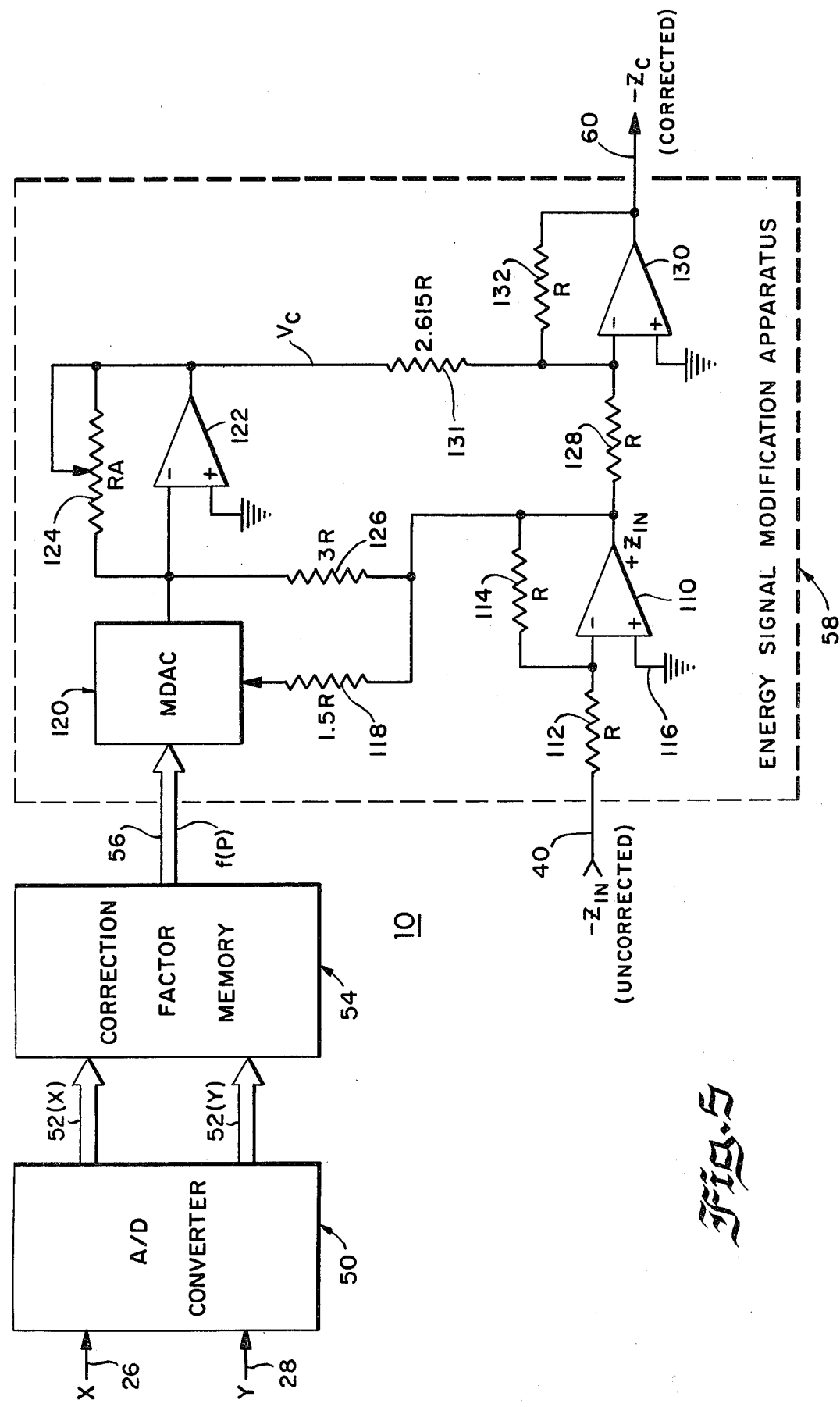
FIG. 5 is a block diagram and schematic representation of the on-line energy correction apparatus of FIG. 1.

Turning now to a detailed discussion of the on-line energy correction apparatus 10 and referring now to FIG. 5, on an image event by image event basis, the Xa and Ya coordinate positions of each image event are utilized to address and read out the corresponding correction factor f(P) for the pixel area corresponding to the image event from the energy correction factor memory 54. The energy signal modification circuit 58 of the energy correction apparatus responds to the readout f(P) and modifies the uncorrected energy signal $Z_{IN}$ at 40 to produce a corrected $Z_c$ signal at 60.

Before considering the detailed operation of the on-line energy correction apparatus 10 of FIG. 5, the circuit parameters and interrelationships of the energy signal modification circuitry 58 will be discussed to evaluate the operation of the energy signal modification circuit 58 with respect to the calculated and stored f(P).

The energy signal modification circuitry 58 in a specific embodiment includes an operational amplifier 110 having an inverting input connected through a resistor 112 to the uncorrected $Z_{IN}$ energy signal 40. A feedback resistor 114 is connected between the output of the operational amplifier 110 and the inverting input. The non-inverting input of the amplifier 110 is connected to a ground reference potential 116. The resistance values of resistors 112 and 114 are equal and denoted as R. Thus, the amplifier 110 is an inverting amplifier with a gain of unity. The output of the amplifier 110 is connected through a resistor 118 of component value 1.5R to an analog reference supply input of a multiplying D to A converter 120 (hereinafter MDAC).

The digital input of the MDAC 120 is connected to the correction factor f(P) at output 56 of the energy correction factor memory 54. The analog output of the MDAC 120 is connected to an inverting input of an operational amplifier 122. A feedback resistor 124 of component value $R_A$ is connected between the output and the inverting input of the amplifier 122. A non-inverting input of the amplifier 122 is connected to the ground reference potential 116. A resistor 126 of component value 3R is connected between the inverting input of the amplifier 122 and the output of the amplifier 110. The output of the amplifier 110 is also connected through a resistor 128 of component value R to an inverting input of an operational amplifier output stage 130. The non-inverting input of the amplifier 130 is connected to the ground reference potential 116. The inverting input of the amplifier 130 is also connected through a resistor 131 of component value 2.615R to the output of the amplifier 122 designated as $V_C$. A feedback resistor 132 of value R is connected between the output of the amplifier 130 and the inverting input of the amplifier 130. The output 60 of the amplifier 130 provides the $Z_C$ corrected energy signal that is supplied to the window analyzer 48 of FIG. 1. At the output of the MDAC 120, the output current is designated as $I_o$.

With the above defined parameters of a specific embodiment of the on-line energy correction apparatus 10 and the energy signal modification circuitry 58, the following analysis establishes the relationship between the correction factor variable f(P)', the corrected energy signal $Z_C$ at 60, and the uncorrected energy signal $Z_{IN}$ at 40 to provide the desired modification relationship to correct the image event energy input signals at 40 by accounting for the non-uniformities of the energy response of the camera and providing the corrected energy output signals $Z_C$ at 60. (For circuit parameter calculation and analysis purposes as discussed hereinbefore, the correction factors f(P) are stored in the range of 0 to 255 in a preferred embodiment and are evaluated in the following relationships as the variable f(P)' with the range 0 to 255 to allow a center uncorrected value of zero for f(P)' which corresponds to a value of f(P) of 128 at the center of the range 0 to 255 as stored):

$$-128 \leq f(P)' \leq 127 \quad (4)$$

$$I_o = -\frac{f(P)' + 128}{256} \cdot \frac{Z_{IN}}{1.5R} \quad (5)$$

$$V_c = -R_A \left( -\frac{f(P)' + 128}{256} \cdot \frac{Z_{IN}}{1.5R} + \frac{Z_{IN}}{3R} \right) \quad (6)$$

$$V_c = R_A \frac{f(P)' Z_{IN}}{(256)(1.5R)} \quad (7)$$

$$-Z_{OUT} = -Z_c = Z_{IN} + \frac{V_c}{2.615} = Z_{IN} + \frac{f(P)' Z_{IN} R_A}{(256)(1.5R)(2.615)} \quad (8)$$

$$-Z_{OUT} = -Z_c = Z_{IN}\left[ \frac{(1 + f(P)' R_A)}{(256)(1.5R)(2.615)} \right] \quad (9)$$

Thus, to find f(P)' so that $Z_{OUT} = Z_c = Z_{IN}$ for $Z_{Ref}$ at the reference level of PMT19, $Z_{19} = 0$ (corresponding to a zero, correction factor);

$$Z_{19} = 0 = Z_{IN} + \frac{Z_{IN} f(P)' R_A}{1004 R} \quad (10)$$

Solving for f(P)';

$$f(P)' = \frac{Z_{19} - Z_{IN}}{Z_{IN}} \cdot \frac{1004}{R_A/R} \quad (11)$$

Thus, if f(P)' is to be calculated according to relationsip (2), $R_A/R$ will be chosen or adjusted in the energy signal modification circuit 58 such that $(R_A/R) = 1.004$. If the range of stored correction factors f(P) is 0 to 255 with a center range zero correction value of 128;

$$f(P) = f(P)' + 128 \quad (12)$$

$$\text{With } f(P) = \left[ \frac{Z_{19} - Z_{IN}}{Z_{IN}} \cdot \frac{1004}{R_A/R} \right] + 128 \quad (13)$$

$$\text{and with } R_A/R = 1.004; f(P) = \left[ \frac{Z_{19} - Z_{IN}}{Z_{IN}} \right] \cdot 1000 + 128 \quad (14)$$

Thus, the relationships of (2) and (14) are in agreement for the calculation and storage of the correction factor f(P) and the use of the correction factor f(P) by the energy signal modification circuit 58 to modify the image event signals $Z_{IN}$. When an image event occurs, the corresponding $Z_{IN}$ uncorrected energy signal at 40 is processed by the energy signal modification circuit 58. The f(P) correction factors are read out of the energy correction factor memory 54 in accordance with the X,Y coordinate position of the image event corresponding to the $Z_{IN}$ signal to provide a correction factor signal at the output of the MDAC 120 scaled according to the value of the image event energy signal $Z_{IN}$. The output of the MDAC 120 is then processed through the amplifier 122 to the output $V_c$. The $V_c$ signal is then summed with the $Z_{IN}$ signal at the inverting input of the amplifier 130; the $V_c$ signal being scaled by the resistor 2.615R. Thus, the correction factor f(P) is scaled by the actual energy of the image event and added to the energy of the image event signal $Z_{IN}$ to provide a corrected energy output signal $Z_c$ in proportion to the input signal and modified by the correction factor f(P).

Thus, the on-line energy correction apparatus 10 corrects the input image event energy signal on an event by event basis according to the non-uniform energy response of the camera and provides the corrected energy signal $Z_c$ to be analyzed by the window analyzer 48 to decide whether the image event is to be accepted or rejected.

Accordingly, the energy signals of each image event are not changed in value by the on-line correction apparatus 10 to the mean energy level of the reference pixel energy or the mean level of the pixel area in which the image event occurred, but are instead corrected proportionally only to the extent of the non-uniform camera response. The window analyzer 48 in accordance with the set energy window then performs the decision process on the image event energy signal normalized for a uniform camera response; a valid image event being accepted if the $Z_c$ signal is within the energy window or being rejected if the $Z_c$ signal is outside the energy window.

It can also be seen that the on-line energy correction apparatus 10 may be utilized with a radiation source having multiple energy levels with the on-line correction apparatus 10 applying energy correction factors to the image events having energy signals in the various ranges of energy levels. The corrected energy output signal $Z_c$ at 60 is provided to window analyzers 48, 90, 92, etc . . . having set energy windows of the desired multiple source energy level; for example, a window analyzer having a predetermined set energy window being provided for each energy level of the multiple energy level source. Further, the on-line energy correction apparatus 10 automatically provides corrected energy signal outputs $Z_c$ for image events resulting from sources of different energy levels without modification to the scintillation camera or the on-line energy correction apparatus; for different energy level sources, appropriate window analyzers being provided to detect the corrected energy signal $Z_c$.

While there has been illustrated and described several embodiments of the present invention, it will be apparent that various changes and modifications thereof will occur to those skilled in the art. For example, the preferred embodiment of the energy modification circuit 58 exhibits accurate linearity response and stable operation for various operating conditions, but it should be understood that in other specific embodiments various other digital and analog computers and function generation are utilized to provide an energy correction of the image event signal $Z_{IN}$ according to the general relationship $Z_c = Z_{IN}(1 + f(P)')$. For example, a digital computer could be utilized to perform the energy signal modification according to the stored correction factor of the image field including interpolation of the stored correction factor dependent on the image event position.

It should also be realized that in specific embodiments, the correction factors f(P) are stored in various formats and ranges and can be modified with devices other than a multiplying digital to analog converter.

Accordingly, it is intended in the appended claims to cover all such changes and modifications as fall within the true spirit and scope of the present invention.

I claim:

1. Correction apparatus for a scintillation camera, the scintillation camera providing image event position coordinate data and image event energy signals for each image event that occurs during on-line use of the scintillation camera, the correction apparatus comprising:
   memory means having stored therein correction factors in an addressable data array format, said correction factors representing the non-uniformity of the energy response of the scintillation camera as a function of image event position over the image field of the scintillation camera;
   means responsive to the image event coordinate position signal of each image event to control the memory means to read out the correction factor corresponding to each image event; and
   image event energy signal correction means responsive to the uncorrected image event energy signal for scaling said read-out correction factor and using said scaled correction factor for generating a corrected image event energy signal.

2. The correction apparatus of claim 1 wherein said image event energy signal correction means comprises means for multiplying the read-out correction factor by the image event energy signal, and means for combining the image event energy signal and the product of the image event signal and the read-out correction factor to provide the corrected image event energy signal.

3. The correction apparatus of claim 2 wherein said correction factors are in a digital format, and said multiplying means comprises a multiplying digital to analog converter having said read-out correction factor as a digital input and the image event energy signal as a multiplying analog reference input, said combining means having said image event energy signal and the output of said multiplying digital to analog convertor as inputs.

4. The correction apparatus of claim 1 wherein said stored correction factors are determined during an off-line test, measurement and analysis phase.

5. The correction apparatus of claim 4 wherein said off-line test, measurement and analysis phase calculates the correction factors by measuring the energy distribution of the scintillation camera from a field flood source as a function of image array position.

6. The correction apparatus of claim 5 wherein said energy distribution data of said off-line test, measurement and analysis phase is utilized to calculate said correction factors by accumulating the total number of image events in each elemental positional array area, accumulating the total energy signals of the image events in each elemental positional array area, dividing the total energy signals by the total number of image events to obtain an average image event energy signal represented by $Z_{map}$ for each elemental positional array area, and calculating the correction factors of f(P) for each elemental positional array area as a relationship between the average energy $Z_{map}$ and the average energy for a reference elemental position array area.

7. The correction apparatus of claim 1 wherein said scintillation camera includes an image event energy window analyzer having a fixed width energy window, said corrected image event energy signal being connected to said image event window analyzer.

8. The correction apparatus of claim 1 wherein said scintillation camera includes a plurality of fixed width image event window analyzers, each of said window analyzers having a fixed width energy window for measuring a different image event energy signal level, said corrected image event energy signal being connected to said plurality of image event window analyzers, said image event energy signal correction means being operative to correct scintillation camera non-uniformities for image events orginating from a multiple level energy source.

9. The correction apparatus of claim 1 wherein said correction factors are stored in said memory means in a digital data format having a range from 0 to $2^N$ with the center of the digital range corresponding to a correction factor of zero to be applied to the image event energy signal and representing the energy response of the scintillation camera at a reference position in the image field.

10. A method for correcting image event energy signals in a scintillation camera for the non-uniform energy response of the scintillation camera and as a function of image field position of the image event, the scintillation camera providing an image event position coordinate signal and an image event energy signal in response to each image event that occurs, the method comprising:

determining an array of correction factors during an off-line test, measurement and analysis phase by measuring the energy response of the scintillation camera to a field flood source, the correction factors defining the variation in energy response of the scintillation camera as a function of position in the image field;

storing said determined correction factors for use during an on-line diagnostic phase of the scintillation camera;

reading out the correction factor that corresponds to each image event position coordinate signal during the on-line diagnostic phase;

scaling the read-out correction factor for each image event in accordance with the uncorrected image event energy signal; and correcting the image event energy signal for each image event in accordance with the corresponding scaled readout correction factor to provide a corrected image event energy signal.

* * * * *